United States Patent [19]
Scheremet et al.

[11] Patent Number: 5,160,322
[45] Date of Patent: Nov. 3, 1992

[54] OCCLUSIVE CHEST SEALING VALVE

[75] Inventors: William Scheremet, Minneapolis; Martin W. Van Buren, Coon Rapids, both of Minn.

[73] Assignee: Brunswick Biomedical Technologies, Inc., Wareham, Mass.

[21] Appl. No.: 852,360

[22] Filed: Mar. 17, 1992

Related U.S. Application Data

[63] Continuation of Ser. No. 662,779, Feb. 28, 1991, abandoned.

[51] Int. Cl.⁵ ............................................. A61M 1/00
[52] U.S. Cl. ................................... 604/122; 128/887
[58] Field of Search ............... 604/122, 126, 304, 307, 604/308; 128/888, 887, 889; 137/533.21, 533.27, 543.15

[56] References Cited

U.S. PATENT DOCUMENTS 4,465,062  8/1984  Versaggi et al. ............... 604/122 X
4,717,382  1/1988  Clemens et al. ............... 604/122 X Primary Examiner—John J. Wilson
Assistant Examiner—Jeffrey A. Smith
Attorney, Agent, or Firm—John W. Adams

[57] ABSTRACT

A one-way valve for use in the emergency closing of an open thoracic wound to prevent inflow of air into the thoracic cavity but permitting one-way outlet flow of air and liquid from the cavity thus preventing pressure build up within the thoracic cavity.

4 Claims, 2 Drawing Sheets

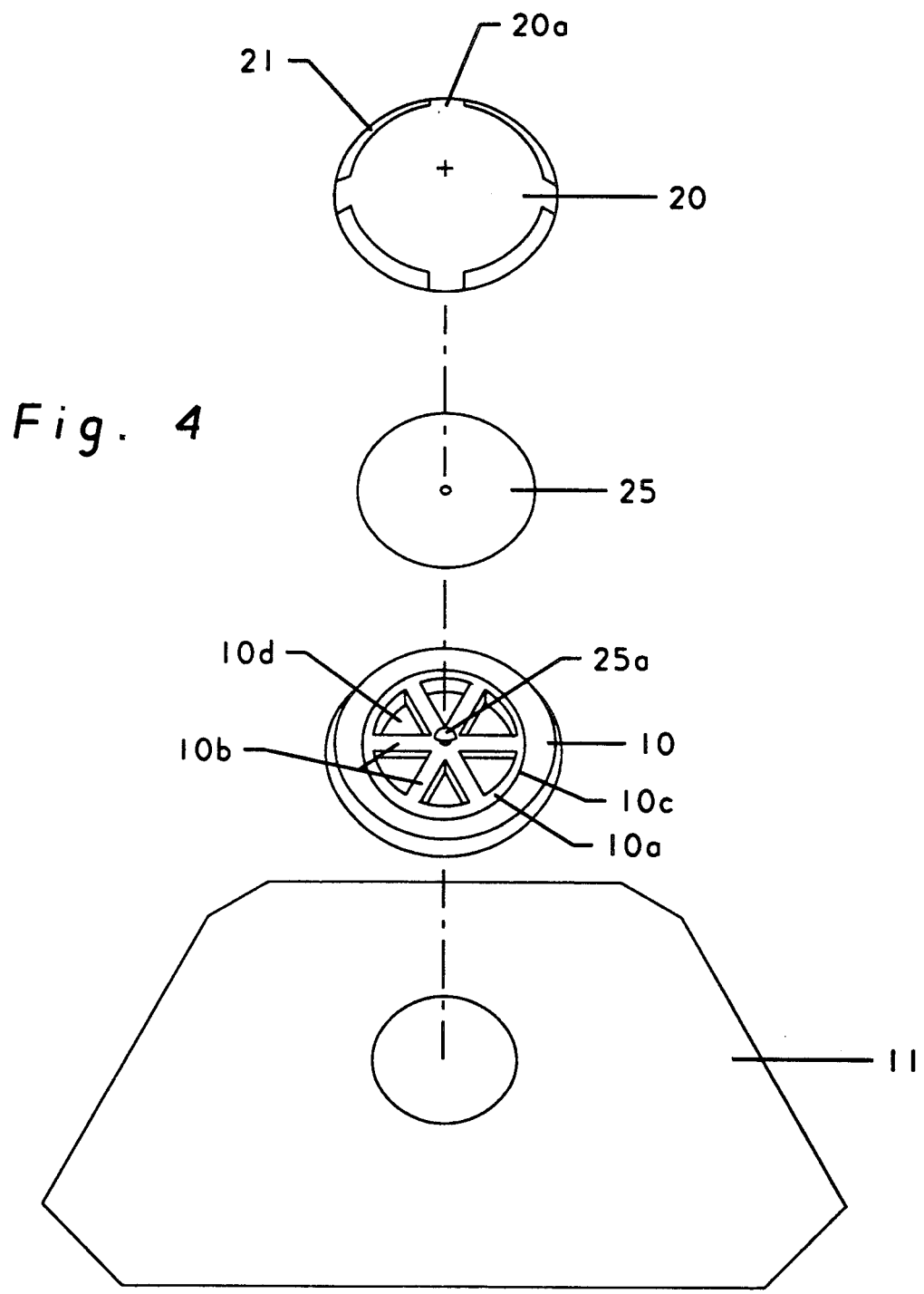

OCCLUSIVE CHEST SEALING VALVE

This application is a continuation of applicants' previously filed U.S. patent application Ser. No. 07/662,779filed Feb. 28, 1991, now abandoned also entitled: OCCLUSIVE CHEST SEALING VALVE.

BACKGROUND OF THE INVENTION

In normal breathing, the muscles of the rib cage and diaphragm contract, increasing the size of the chest cavity. The lungs inflate because of the negative pressure that is created in the lungs as the chest volume increases. This causes air to flow into the lungs. When the diaphram and rib cage relax, decreasing the size of the chest cavity, the air is passively expelled from the lungs. The lungs are prevented from collapsing by a negative pressure which exists in the pleural space, that is the potential space between the parietal and visceral pleuras.

When the chest wall sustains a penetrating wound as from a gun shot or knife, the wound opening creates a path for outside air to flow into the chest cavity. This flow of external atmospheric air into the chest cavity eliminates the negative pressure which normally exists in the pleural space. As a result, the lungs cannot inflate properly, because the chest defect allows the air which has been drawn into the chest cavity to equalize the pressure therein with the atmospheric pressure. The presence of the atmospheric air in the chest may also introduce contaminates into the chest cavity.

At the present time, one of the treatment procedures is to provide an occlusive dressing large enough to overlap the wounds' edges and to tape it securely on all four sides so as to seal the wound and prevent air from passing into the chest cavity through the wound. This permits the patient to breath without building up pressure within the cavity unless the lung has been punctured or torn. If the lung has been penetrated, air will be drawn into the chest cavity through that penetration and produce a pressure build-up within the chest cavity if the wound has been sealed externally. In order to overcome this problem under the emergency conditions in the field, the American College of Surgeons recommends the taping of the occlusive dressing on only three sides so that if pressure is building up within the chest cavity, this pressure may be discharged through the open side of the dressing. Unfortunately, however, the conditions surrounding the emergency treatment of the patient may neutralize the valve effect of this type of dressing application. These conditions include the application of a spine board, other pressure dressings, cot-restraint belts and the specific location of the wounds relative to the patient's position during transport. Frequently, the patient also will have to be moved into a position, or external restraining or support apparatus applied to the patient which will interfere with the operation of the valve effect of the open side of the dressing.

The problem for the emergency staff during the early treatment of such wounds is to monitor the patient and prevent, if possible, the build-up of pressure within the chest cavity, even when one of the lungs has been penetrated. This is an extremely difficult problem to solve when there are a great many other demands on the attendant. Frequently, it is necessary to use a pressurized oxygen device to force uninjured lungs to inflate. This device, however, has the potential of increasing the damage to an injured lung by forcing high pressure air through the opening or defect in that lung. This pressurization through the lungs may further increase the pressure in the chest cavity if the chest opening or defect is sealed.

One of the most important life threatening conditions that must be prevented is sufficient build up of pressure within the chest cavity making it impossible for the lung to inflate, thus collapsing the lung. This pressurized condition within the chest cavity also compresses the heart and reduces its ability to function. This invention provides a valve controlled release opening to prevent this pressure build up in the chest cavity.

SUMMARY OF THE INVENTION

This invention provides a one-way control valve for emergency adhesive application to the chest of a patient having a wound opening which has penetrated the chest wall. The one-way valve permits air and liquid to pass outwardly from the cavity but closes the same against the flow of atmospheric air into the chest cavity. Release of this pressure prevents the creation of a life threatening condition within the chest cavity by maintaining a sub-atmospheric condition within the cavity required for lung inflation. In addition, this device may be used during pressurized mechanical ventilation without adding to the risk of a tension pneumothorax. Normally, a negative pressure exists within the chest cavity. Imposing a positive pressure within the cavity creates an immediate life threatening condition that must be corrected as soon as possible.

This invention provides a flexible pressure sensitive adhesive attachment panel for attaching the release valve over the penetrating wound to prevent pressure build up in the chest cavity.

DETAILED DESCRIPTION OF THE DRAWINGS

DETAILED DESCRIPTION OF THE PREFERRED EMBODIMENT

The drawings illustrate a valve assembly embodying the invention. This valve includes a rigid annular base member 10 which is permanently secured a flexible attachment member 11, which in the form shown consists in a panel or sheet made from suitable transparent flexible plastic material having a transparent pressure sensitive adhesive coating 12 on the bottom surface thereof.

The flexible attachment panel 11 must be sufficiently large and have sufficient stiffness to prevent it from being drawn into a penetrating thoracic wound. Flexibility is important to permit the panel to conform to the irregularities of the outer surface of the patient's chest. The panel should also be transparent, so that the valve can be visually positioned with its base surrounding the outside of the wound to sealingly enclose the same. A number of different clear plastic films are suitable such as are manufactured by Molco, of Waymart, Pa.

Figure 1:
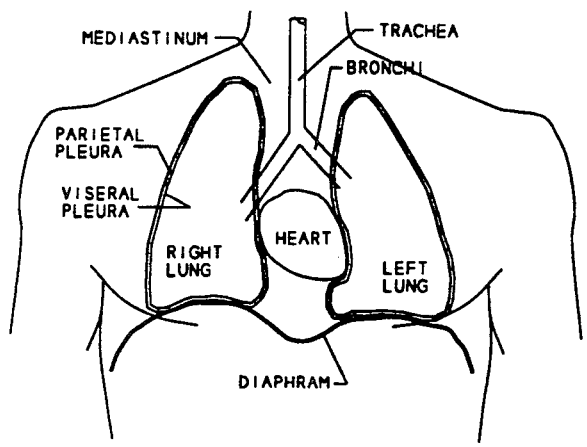
FIG. 1 is a view showing the chest cavity with the basic anatomical components housed therein.
Figure 2:
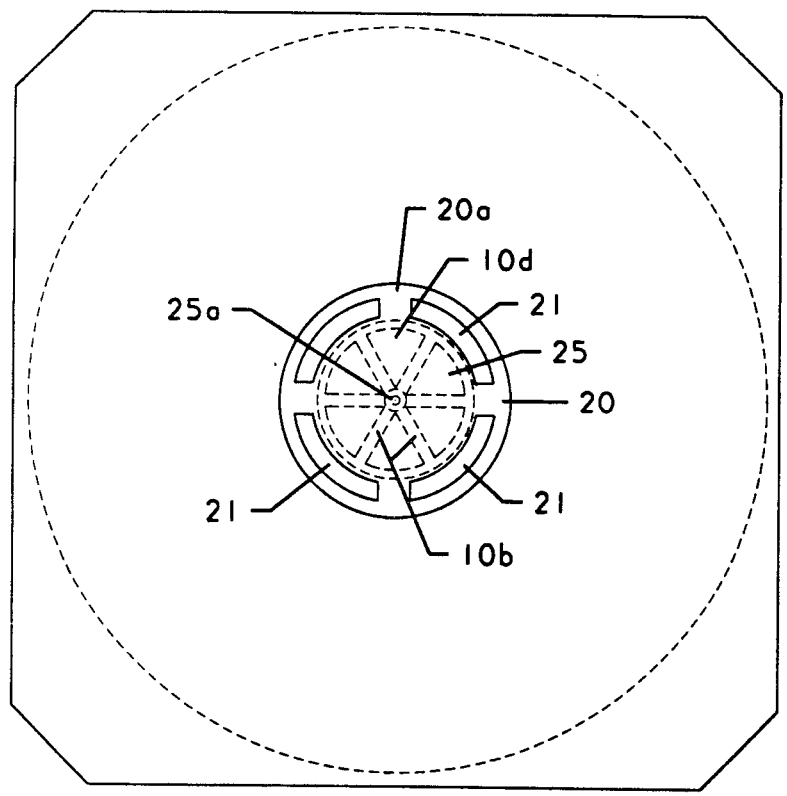
FIG. 2 is a top plan view of a check valve assembly embodying the invention.
Figure 3:
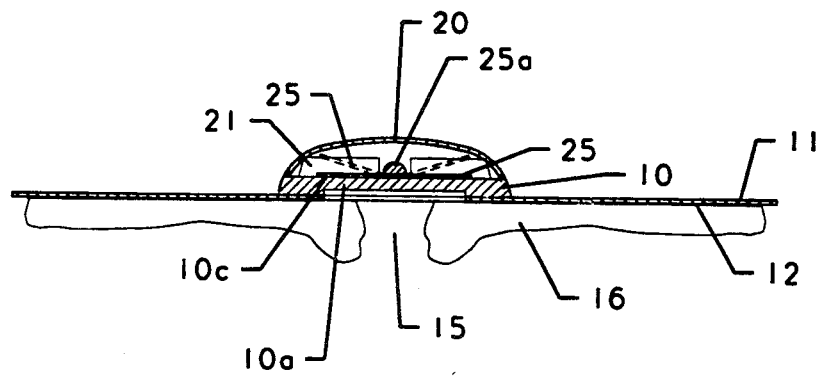
FIG. 3 is a central vertical sectional view through the check valve assembly of FIG. 2; and, FIG. 4 is an exploded perspective view of the check valve assembly.

The wound 15 is shown diagramatically in FIG. 3 with the surrounding skin layer designated by the numeral 16. The adhesive must, of course, be hypo-allergenic, be resistant to the presence of blood, moisture, and other body fluids, and remain active under temperature variations encountered at the, scene of the injury. Furthermore, the adhesive should also permit removal of the panel and valve assembly without leaving significant amounts of adhesive residue on the patient's skin surface. A suitable adhesive is manufactured by 3-M Company of St. Paul, Minn., and is used on their 3-M Stoma Seal 1500 product.

The base 10 is made from suitable rigid transparent material such as a suitable rigid plastic material and has a valve housing 20 fixed thereon in spaced relation thereabove. In the form shown, the housing 20 is dome shaped with spaced cut out openings 21 which form support struts 20a around the periphery thereof. The spaced struts 20a are connected in fixed relation to the annular base member 10 and support the housing dome 20 on the annular base 10. The openings 21 around the top of the base 10 permit air, blood, and body fluids to escape through the wound opening 15.

In the form shown, a valve element 25 is made from highly flexible thin material such as latex or vinyl and in the form shown is generally circular in shape with its center attached to the center of a supporting spider frame 10a as by a post or rivet 25a. The spider frame 10a is fixed across the opening defined by the annular base member 10. The valve disc 25 is connected at its center to the center of spokes 10b to the supporting spider frame 10a to maintain the valve disc 25 in alignment with its annular valve seat 10c extending around the inside of the lower portion of the central opening defined within the annular base member 10. The valve element 25 is shown in closed seated position in FIG. 4. In its closed position, the valve disc seals against the planar annular seat 10c with intermediate support being provided by the spokes 10b of the frame 10a. Openings 10d defined between the spokes 10b permit air and fluids to pass out from the chest cavity to prevent pressure from building up within the cavity. The dome 20 protects the valve against contact from objects that would interfere with its opening and closing action.

What is claimed is:

1. A closure valve for attachment to the outer skin surface surrounding an open chest cavity wound of a patient comprising:
   a one-way check valve assembly including,
      an annular rigid base having an inside and an outside and defining an opening therethrough and adapted to surround the wound of a patient,
      a valve seat formed on the outside of said annular base.
   attachment means having pressure-sensitive adhesive on the inside thereof and including an opening therein for surrounding the wound of a patient when attached,
   means for securely attaching said annular base to the attachment means with the openings therein in substantial axial alignment to permit the base member to be securely attached to the body of a patient with the wound opening substantially centered within the aligned openings of the base and the attachment means,
   a generally flat check valve mounted on the top of said base in registration with the opening through the base,
   means for attaching said check valve to said base member in a manner to permit the valve to prevent backflow of fluid through the opening but permitting the discharge of fluid outwardly through the opening to maintain a negative pressure within the chest cavity communicating with the body wound,
   the valve and base assembly being relatively thin and defining a top surface disposed in closely spaced relation above the attachment means surrounding the wound opening of a patient when attached to the patient,
   a protective cover housing fixed in spaced relation above the base member and having openings therein to permit air and body fluids passing through the valve to escape from the wound, the lower edges of the openings lying in a plane defined generally by the base member and valve seat provided thereby to prevent any build-up of fluids under the housing outside of the valve.

2. A closure valve for attachment to the outer skin surface surrounding an open chest cavity wound of a patient comprising:
   a one-way check valve assembly including,
      an annular rigid base having an inside and an outside and defining an opening therethrough and adapted to surround the wound of a patient, a valve seat formed on the outside of said annular base.
   attachment means having pressure-sensitive adhesive on the inside thereof and including an opening therein for surrounding the wound of a patient when attached,
   means for securely attaching said annular base to the attachment means with the openings therein in substantial axial alignment to permit the base member to be securely attached to the body of a patient with the wound opening substantially centered within the aligned openings of the base and the attachment means,
   a generally flat check valve mounted on the top of said base in registration with the opening through the base,
   means for attaching said check valve to said base member in a manner to permit the valve to prevent backflow of fluid through the opening but permitting the discharge of fluid outwardly through the opening to maintain a negative pressure within the chest cavity communicating with the body wound,
   the valve and base assembly being relatively thin and defining a top surface disposed in closely spaced relation above the attachment means surrounding the wound opening of a patient when attached to the patient,
   a protective cover housing fixed in spaced relation above the base member and having openings therein to permit air and body fluids passing through the valve to escape from the wound, the lower edges of the openings lying in a plane defined generally by the base member and valve seat provided thereby to prevent any build-up of fluids under the housing outside of the valve,
   said attachment means comprising a flexible flat attachment panel with an opening therein surrounding the wound opening of a patient for sealingly attaching the valve to the patient in wound surrounding position to sealingly enclose the wound and to control flow therethrough, wherein the valve constitutes a flat light-weight flexible disc preventing backflow of fluid through the inlet opening, and a valve chamber surrounding the valve disc and maintaining operational registration of the disc with the valve seat.

3. The structure set forth in claim 2, wherein the cover housing is raised above the valve to provide operational clearance for the valve, and discharge openings being provided around the outer periphery of the cover housing to permit substantially unrestricted discharge flow from the valve through the area under the housing.

4. The structure set forth in claim 2 and a valve supporting spider frame wherein the valve is supported thereon when in closed position but providing openings to permit the discharge of air and fluid outwardly through the valve from the chest cavity.

* * * * *